(12) United States Patent
Gautier et al.

(10) Patent No.: US 6,517,850 B1
(45) Date of Patent: Feb. 11, 2003

(54) INSECT CONTROL METHOD USING 1-PHENYLPYRAZOLES OR 1-HETEROARYLPYRAZOLES

(75) Inventors: Martine Gautier, Limonest (FR); Jean Derois, Saint Cyr au Mont d'Or (FR)

(73) Assignee: Rhone-Poulenc Agrochimie, Lyons (FR)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/983,074

(22) PCT Filed: Jun. 26, 1996

(86) PCT No.: PCT/FR96/00993

§ 371 (c)(1),
(2), (4) Date: Jun. 11, 1998

(87) PCT Pub. No.: WO97/01278

PCT Pub. Date: Jan. 16, 1997

Related U.S. Application Data

(60) Provisional application No. 60/007,747, filed on Oct. 13, 1995, now abandoned.

(30) Foreign Application Priority Data

Jun. 29, 1995 (FR) .............................. 95 08073

(51) Int. Cl.$^7$ .............................. A01N 25/02
(52) U.S. Cl. .................. 424/405; 514/407; 424/84; 424/409
(58) Field of Search .................. 424/405, 407, 424/408, 409, 417, 84; 514/407

(56) References Cited

U.S. PATENT DOCUMENTS

| | | | |
|---|---|---|---|
| 4,812,309 A | 3/1989 | Ong .............................. 424/84 |
| 5,021,237 A | 6/1991 | Bruey .......................... 424/43 |
| 5,232,940 A | 8/1993 | Hatton et al. ................. 514/407 |
| 5,306,694 A | 4/1994 | Phillips et al. ............... 504/253 |
| 5,451,598 A | 9/1995 | Salmon ....................... 314/404 |
| 5,496,845 A * | 3/1996 | Martin et al. ................ 514/427 |
| 5,547,974 A | 8/1996 | Hatton et al. ................ 514/406 |
| 5,567,429 A | 10/1996 | Senbo ......................... 424/405 |
| 5,614,182 A * | 3/1997 | Davidson et al. ............. 424/84 |
| 5,939,441 A | 8/1999 | Stetter et al. |
| 6,060,497 A * | 5/2000 | Kodama et al. ............. 514/404 |

FOREIGN PATENT DOCUMENTS

| | | |
|---|---|---|
| AU | 552549 | 6/1986 |
| EP | 0084310 | 7/1983 |
| EP | 0190844 | 8/1986 |
| EP | 0212226 | 3/1987 |
| EP | 0254257 | 1/1988 |
| EP | 0295117 | 12/1988 |
| EP | 0430634 | 6/1991 |
| EP | 0500209 | 8/1992 |
| EP | 0679650 A1 | 11/1995 |
| FR | 2713889 | 6/1995 |
| WO | 87/03781 | 7/1987 |
| WO | 92/14363 | 9/1992 |
| WO | 93/06089 | 4/1993 |
| WO | 94/21606 | 9/1994 |
| WO | 95/22902 | 8/1995 |

OTHER PUBLICATIONS

Database WPI, Week 8627, Derwent Publications Ltd., London, GB, AN 86–173308 (abstract of JP 61–106505), 1986.

* cited by examiner

*Primary Examiner*—Neil S. Levy
(74) *Attorney, Agent, or Firm*—Burns, Doane, Swecker & Mathis, L.L.P.

(57) ABSTRACT

Insecticidal compositions comprising:
a) between 0.001 and 5%, preferably between 0.05 and 0.5%, of a solid compound of 1-phenylpyrazole type, in particular 1-[2,6-$Cl_2$-4-$CF_3$-phenyl]-3-CN 4-[SO-$CF_3$]-5-$NH_2$ pyrazole; and
b) between 0.05 and 10%, preferably between 0.1 and 5%, of a thickener; and
c) between 5 and 50%, preferably between 10 and 40%, of propylene glycol, the compound of formula (I) being in the dissolved state in the said propylene glycol.

Method for controlling insects using this composition, in particular for controlling ants.

35 Claims, No Drawings

INSECT CONTROL METHOD USING 1-PHENYLPYRAZOLES OR 1-HETEROARYLPYRAZOLES

CROSS-REFERENCE TO RELATED APPLICATION

This application is the U.S. national stage of International Application No. PCT/FR96/00993, filed Jun. 26, 1996 and designating the United States, which was published by the International Bureau in French, not in English, on Jan. 16, 1997 as WO 97/01278, and which claims the priority of United States Provisional Application No. 60/007,747, filed Oct. 13, 1995, now abandoned.

The present invention relates to novel compositions intended for controlling insects, and to a control method using the said compositions.

Insecticidal compounds of the phenylpyrazole type which may be used for controlling insects are known, in particular from patent applications EP 295,117, WO 87/3781, 93/6089 and 94/21606. EP 295,117 also mentions compositions in the form of edible baits comprising from 0.01% to 5% of such active materials.

It is often desirable to place such baits in areas in which undesirable insects are liable to circulate, in particular when these insects are ants, cockroaches, wasps and termites, and most particularly insects which travel in a group or in columns such as ants. The areas concerned may in particular include living quarters or areas outside these quarters such as patios or pleasure gardens or passageways.

When it is desired to apply the compositions in the form of liquid baits, it is convenient to distribute these baits in the form of drops, and it is desirable for these drops to remain where they are.

More particularly, when it is desired to apply these compositions in the form of drops, it is desirable for the said drops to remain where they are for the longest possible period, in order for the insects to be able to come effectively into contact with these compositions, and to ingest them as much as possible. In the sense of the present invention, the term drop means a volume of rounded shape of between 0.01 and 1 ml, preferably between 0.01 and 0.1 ml, whose height, for an isolated drop on a flat surface, is greater than 1 mm, preferably greater than 3 mm.

Such an application then poses a certain number of difficulties.

It is thus necessary for these drops to disappear as slowly as possible, in particular by spreading or by evaporation.

On account of the diverse nature of the supports on which these drops may be deposited, it is also necessary for them not to be absorbed too rapidly, for example in the case of porous supports.

In the case of multiple applications from a single storage container, it is also desirable for the insecticidal composition to retain its performance despite repeated opening and closing of the packaging.

One aim of the invention is to overcome these difficulties in total or in part.

Another aim of the invention is to propose advantageous compositions for application by deposition of drops.

Another aim of the invention is to provide compositions comprising at least one insecticidal active material of phenylpyrazole type which is applicable in drop form, in particular under conditions favouring the evaporation or absorption of liquids.

Another aim of the invention is to provide compositions which are attractant and nourishing for insects, especially for gregarious insects and/or insects which live in a society such as ants, these compositions comprising at least one insecticidal active material of phenylpyrazole type.

Another aim of the invention is to propose insecticidal compositions which retain their performance in the course of repeated use, in particular in the course of frequent opening of the packages containing them.

It has now been found that these aims could be achieved, in total or in part, using the control compositions and method according to the invention which are described in detail below. It is pointed out that the percentages indicated in the present text are weight/weight percentages, except where specifically indicated otherwise.

The subject of the present invention is thus, firstly, insecticidal compositions comprising:

a) between 0.001 and 5%, preferably between 0.05 and 0.5%, of a compound of formula (I):

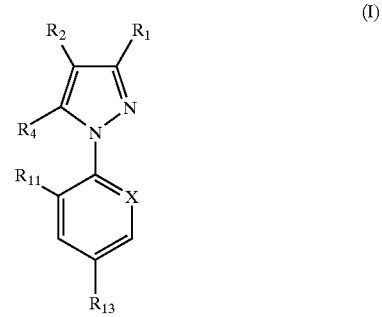

in which:
- $R_1$ is a halogen atom or a CN or methyl group;
- $R_2$ is $S(O)_n R_3$;
- $R_3$ is alkyl or haloalkyl;
- $R_4$ represents a hydrogen or halogen atom; or a radical $NR_5R_6$, $S(O)_m R_7$, $C(O)R_7$ or $C(O)O—R_7$, alkyl, haloalkyl or $OR_8$ or a radical $—N=C(R_9)$ $(R_{10})$;
- $R_5$ and $R_6$ independently represent a hydrogen atom or an alkyl, haloalkyl, C(O)alkyl or $S(O)_r CF_3$ radical; or $R_5$ and $R_6$ may together form a divalent alkylene radical which may be interrupted by one or two divalent hetero atoms, such as oxygen or sulphur;
- $R_7$ represents an alkyl or haloalkyl radical;
- $R_8$ represents an alkyl or haloalkyl radical or a hydrogen atom;
- $R_9$ represents an alkyl radical or a hydrogen atom;
- $R_{10}$ represents a phenyl or heteroaryl group optionally substituted with one or more halogen atoms or groups such as OH, —O-alkyl, —S-alkyl, cyano or alkyl;
- $R_{11}$ and $R_{12}$ represent, independently of each other, a hydrogen or halogen atom;
- $R_{13}$ represents a halogen atom or a haloalkyl, haloalkoxy, $S(O)_q CF_3$ or $SF_5$ group;
- m, n, q and r represent, independently of each other, an integer equal to 0, 1 or 2;
- X represents a trivalent nitrogen atom or a radical $C—R_{12}$, the other three valency positions of the carbon atom forming part of the aromatic ring;
- with the proviso that when $R_1$ is methyl, then $R_3$ is haloalkyl, $R_4$ is $NH_2$, $R_{11}$ is Cl, $R_{13}$ is $CF_3$ and X is N;

b) between 0.05 and 10%, preferably between 0.1 and 5%, of a thickener; and c) between 5 and 50%, preferably between 10 and 40%, of propylene glycol, the compound of formula (I) being in the dissolved state in the said composition.

The alkyl radicals in the definition of formula I generally comprise from 1 to 6 carbon atoms. The ring formed by the divalent alkylene radical representing $R_5$ and R6 as well as by the nitrogen atom to which $R_5$ and $R_6$ are attached is generally a 5-, 6- or 7-membered ring.

When the compositions according to the invention are applied in the form of drops deposited in a place where insects, preferably ants, are liable to pass, in particular a place consisting of an absorbent support, the compositions according to the invention are particularly advantageous on account of their slow spreading.

More precisely, the height of a drop of the said compositions above a flat surface on which it is deposited remains advantageously greater than 1 mm, preferably greater than 3 mm, after a period of more than 1 day, preferably of more than 2 days, at ambient temperature.

Furthermore, these compositions are of improved storage in the case where their commercial packaging is frequently opened and closed by the user.

The compositions according to the invention are relatively viscous but, despite this, the active material is uniformly distributed in the composition, by virtue of the nature of this composition.

The compound of formula (I) may be prepared according to one of the methods described in Patent Applications WO 87/3781, 93/6089, 94/21606 and EP 295,117 or alternatively by another method from within the general knowledge of those skilled in the art competent in chemical synthesis. This compound is also referred to in the present text by the term active material.

Among the thickeners which may in particular be used are a heteropolysaccharide, a polyacrylate salt, in particular the ammonium salt, a copolymer of vinylpyrrolidone and vinyl acetate, a polyglycol such as polyethylene glycol, starch or gum arabic.

According to a preferred variant of the composition according to the invention, the composition also comprises from 30 to 70%, preferably from 40 to 60%, of sugars. This composition variant is of considerably enhanced appetency for ants. The sugars are chosen in particular from mono-, oligo- or polyorganosaccharides, especially from sucrose, lactose, fructose, dextrose or glucose, or alternatively molasses or honey.

A preferred class of compounds of formula (1) comprises the compounds where $R_1$ is CN and/or $R_3$ is haloalkyl and/or $R_4$ is $NH_2$ and/or $R_{11}$ and $R_{12}$ are, independently of one another, a halogen atom and/or $R_{13}$ is haloalkyl.

According to a particularly advantageous variant of the invention, the compound of formula (1) used in the invention is 5-amino-3-cyano-1-[2,6-dichloro-4-(trifluoromethyl)phenyl]-4-[(trifluoromethyl)sulphinyl]-1H-pyrazole, which is referred to in the examples by the term "fipronil".

The compositions which form the subject of the invention may also comprise a preserving agent which prevents degradation of the sugar and/or of the thickener, such as sodium benzoate, 1,2-benzisothiazolin-3-one, benzoic acid, parahydroxybenzoic acid and the ester derivatives and alkali metal or alkaline-earth metal salts thereof, in particular the sodium salt, or 2-phenylphenol and the alkali metal or alkaline-earth metal salts thereof, in particular the sodium salt.

Other additives may also be included, such as a dye or an attractant chosen in particular from a flavouring of animal or plant origin, or sodium glutamate.

The nature and dose of the ingredients in the compositions according to the invention are advantageously chosen so that they have a viscosity of between 30 and 10,000 cP, preferably of between 60 and 1000 cP, at ambient temperature. The abbreviation cP denotes a unit of viscosity equal to a centipoise, also equal to one millipascal second (mPa s).

The compositions according to the invention may be prepared simply by mixing the various constituents together, preferably with stirring and while hot.

Faster and more efficient mixing may advantageously be obtained by preparing, in a first step, a premix by dissolving the active material in propylene glycol at ambient temperature in order to do this, optionally with stirring, so as to obtain a solution of concentration substantially equal to 1%. Next, in a second step, the sugar is first of all optionally dissolved in the water with, if necessary, the preserving agent, followed by addition of the thickener which is optionally dissolved with stirring and with heating to a temperature of between 20 and 70° C. In a third step, the active material premix is incorporated into the aqueous solution prepared earlier.

The invention also relates to a method for controlling insects, characterized in that an effective amount of one of the compositions according to the invention is applied to an area in which the insects are liable to be found.

The term effective amount means an amount of composition corresponding to a dose of compound of formula (a) equal to the dose required to destroy at least 90% of the insects concerned, to which the said composition is applied, in a period of between 2 and 15 days, preferably of between 2 and 4 days.

The method according to the invention is preferably used to control ants.

In this case, the effective amount of composition according to the invention corresponds to a dose of compound of formula (1) of between 5 mg and 5 g per 100 $m^2$, preferably of between 10 mg and 2 g per 100 $m^2$.

The area may in particular be in a public or private place, such as living quarters.

In order to carry out the method according to the invention, the composition, also according to the invention, is applied to the area in which the insects are liable to be found, in the form of drops. In this case, the said composition is advantageously packaged in a ready-to-use tube, which the user squeezes in order to obtain the required drops.

According to another variant of the method according to the invention, the composition is placed inside a closed bait box containing openings which are adapted, on account of their size, for the exclusive use of ants or, optionally, of insects of similar size. This variant of the method according to the invention is of improved safety, when it concerns an active material liable to present a risk in the event of accidental contact or ingestion by children or pets.

The examples which follow illustrate the invention without, however, constituting a limitation thereof. In these examples, the compound of formula (I) used is fipronil.

EXAMPLE 1

100 g of a 1% solution of fipronil in propylene glycol, known as the "fipronil premix", are prepared by simple dissolution at ambient temperature.

An aqueous dispersion/solution of 2% of heteropolysaccharide also containing 1% of sodium benzoate, which is denoted by the term "thickener premix", is also prepared by simple mixing.

1000 g of 0.05% fipronil composition are then prepared simply by mixing together the following ingredients used in the proportions indicated:

fipronil premix: 5%
thickener premix: 50%
propylene glycol: 34.9%
blue dye: 0.1%
water: 10%

This composition has a viscosity of 450 cP.

One drop of this composition is deposited in a Petri dish, by squeezing a tube containing the composition prepared above. This drop substantially has the shape of a hemisphere 6 mm in diameter and 4 mm in height. After 2 days, the height of the drop is of the order of 4 mm.

A square receptacle of side length 30 cm is placed in a room at ambient temperature. A layer of soil 5 mm in thickness is placed in the bottom of this container and a test tube which is darkened over part of its length, intended to serve as an ant refuge, containing a pad of cotton wool soaked in water is introduced. A liquid dispenser containing sugary water as a source of food for the ants is also provided. 100 ants (*Lasius niger*) are introduced into this container and are left to acclimatize for 1 week.

A Petri dish into which 4 drops of the composition prepared above have been deposited is then introduced and the liquid dispenser is removed. The drops were deposited by squeezing the tube containing the said composition, and they have substantially the shape of a hemisphere 6 mm in diameter and 4 mm in height.

The results are observed after 4 days. A mortality rate of more than 95% is observed.

EXAMPLE 2

Example 1 is repeated using the following proportions of ingredients:
fipronil premix: 10%
thickener premix: 50%
propylene glycol: 29.9%
blue dye: 0.1%
water: 10%

This composition has a viscosity of 400 cP.
The same results are obtained.

EXAMPLE 3

Example 1 is repeated, preparing 1000 g of composition containing 0.05% fipronil simply by mixing together the following ingredients used in the proportions indicated:
fipronil premix: 5%
thickener premix: 7%
propylene glycol: 5%
sucrose: 50%
blue dye: 0.1%
water: 32.9%

This composition has a viscosity of 300 cP.

One drop of this composition is deposited in a Petri dish, by squeezing a tube containing the composition prepared above. This drop has substantially the shape of a hemisphere 1 cm in diameter and 2 mm in height. After 2 days, the height of the drop is of the order of 2 mm.

As regards the test for application to ants, the test of Example 1 is repeated. The same result is obtained.

EXAMPLE 4

1000 g of composition containing 0.05% of fipronil are prepared by the same procedure as in Example 1.

One drop of this composition, having substantially the shape of a hemisphere 6 mm in diameter and 4 mm in height, is deposited on a horizontal slab, of granular and porous appearance, used for paving a patio.

After 2 days, the height of the drop is of the order of 2 mm.

A tile, cut out of the same material as the above slab and of the same size as the square container of Example 1, is placed at the bottom of this container in place of the layer of soil, and the procedure as in Example 1 is carried out, depositing the 4 drops of composition directly onto this tile.

After 4 days, a mortality rate also of more than 95% is observed for the ants.

EXAMPLE 5

Example 4 is repeated, first depositing the drop of composition onto a flat layer of soil.

After 2 days, the height of the drop is of the order of 1 mm.

The test with the ants is then carried out as in Example 1, but with the 4 drops of composition being deposited directly onto the soil.

After 4 days, a mortality rate which is also of more than 95% is observed.

What is claimed is:

1. A method for controlling ants, said method comprising applying an insecticidally effective amount of an insecticidal composition to an area in which ants are liable to be found, said insecticidal composition comprising:
   (a) between 0.001 and 5% by weight of the compound 5-amino-3-cyano-1-[2,6-dichloro-4-(trifluoromethyl) phenyl]-4-[(trifluoromethyl)sulfinyl]-1H-pyrazole;
   (b) between 0.05 and 10% by weight of a thickener; and
   (c) between 5 and 50% by weight of propylene glycol;
   said compound being in a dissolved state in said composition;
   said insecticidally effective amount of said composition corresponding to a dose of said compound of between 5 mg and 5 g per 100 m$^2$;
   said composition having a viscosity of between 60 and 1000 cP at ambient temperature:
   the percentages by weight being based on the total weight of the composition;
   said composition being applied in the form of drops, the height of a drop of said composition above a flat surface on which said drop is deposited remaining greater than 1 mm after a period of more than 1 day at ambient temperature.

2. A method according to claim 1, wherein said composition is placed inside a closed bait box having openings which are sized for the use of ants.

3. A method according to claim 1, wherein said thickener is selected from the group consisting of a heteropolysaccharide, a polyacrylate salt, a copolymer of vinylpyrrolidone and vinyl acetate, a polyglycol, starch and gum arabic.

4. A method according to claim 1, wherein said composition further comprises from 30 to 70% by weight of sugars.

5. A method according to claim 3, wherein said composition further comprises from 30 to 70% by weight of sugars.

6. A method according to claim 4, wherein said sugars are selected from the group consisting of mono-, oligo- and polysaccharides, molasses and honey.

7. A method according to claim 5, wherein said sugars are selected from the group consisting of mono-, oligo- and polysaccharides, molasses and honey.

8. A method according to claim 4, wherein said composition further comprises a preserving agent which prevents degradation of the sugars and/or of the thickener, said preserving agent being a member selected from the group consisting of sodium benzoate, 1,2-benzisothiazolin-3-one, benzoic acid, parahydroxybenzoic acid and the ester derivatives, alkali metal and alkaline-earth metal salts thereof, and 2-phenylphenol and the alkali metal and alkaline-earth metal salts thereof.

9. A method according to claim 5, wherein said composition further comprises a preserving agent which prevents degradation of the sugars and/or of the thickener, said preserving agent being a member selected from the group consisting of sodium benzoate, 1,2-benzisothiazolin-3-one, benzoic acid, parahydroxybenzoic acid and the ester derivatives, alkali metal and alkali-earth metal salts thereof, and 2-phenylphenol and the alkali metal and alkaline-earth metal salts thereof.

10. A method according to claim 1, further comprising an attractant selected from the group consisting of a flavoring agent of animal origin, a flavoring agent of plant origin and sodium glutamate.

11. A method according to claim 3, further comprising an attractant selected from the group consisting of a flavoring agent of animal origin, a flavoring agent of plant origin and sodium glutamate.

12. A method according to claim 1, wherein said insecticidally effective amount corresponds to a dose of said compound equal to the dose required to destroy at least 90% of the ants in a period of between 2 and 15 days.

13. A method according to claim 3, wherein said insecticidally effective amount corresponds to a dose of said compound equal to the dose required to destroy at least 90% of the ants in a period of between 2 and 15 days.

14. A method according to claim 1, wherein said composition comprises:

(a) between 0.05 and 0.5% by weight of said compound;

(b) between 0.1 and 5% by weight of said thickener; and (c) between 10 and 40% by weight of said propylene glycol.

15. A method according to claim 3, wherein said composition comprises:

(a) between 0.05 and 0.5% by weight of said compound;

(b) between 0.1 and 5% by weight of said thickener; and (c) between 10 and 40% by weight of said propylene glycol.

16. A method according to claim 1, wherein the height of said drop of said composition above a flat surface on which said drop is deposited remains greater than 3 mm after a period of more than 2 days at ambient temperature.

17. A method according to claim 3, wherein the height of said drop of said composition above a flat surface on which said drop is deposited remains greater than 3 mm after a period of more than 2 days at ambient temperature.

18. A method according to claim 14, wherein the height of said drop of said composition above a flat surface on which said drop is deposited remains greater than 3 mm after a period of more than 2 days at ambient temperature.

19. A method according to claim 15, wherein the height of said drop of said composition above a flat surface on which said drop is deposited remains greater than 3 mm after a period of more than 2 days at ambient temperature.

20. A method according to claim 4, wherein said composition comprises from 40 to 60% by weight of sugars.

21. A method according to claim 5, wherein said composition comprises from 40 to 60% by weight of sugars.

22. A method according to claim 6, wherein said sugars are selected from the group consisting of sucrose, lactose, fructose, dextrose and glucose.

23. A method according to claim 7, wherein said sugars are selected from the group consisting of sucrose, lactose, fructose, dextrose and glucose.

24. A method according to claim 12, wherein said insecticidally effective amount corresponds to a dose of said compound equal to the dose required to destroy at least 90% of the ants in a period of between 2 and 4 days.

25. A method according to claim 13, wherein said insecticidally effective amount corresponds to a dose of said compound equal to the dose required to destroy at least 90% of the ants in a period of between 2 and 4 days.

26. A method according to claim 1, wherein said insecticidally effective amount of said composition corresponds to a dose of said compound of between 10 mg and 2 g per 100 $m^2$.

27. A method according to claim 3, wherein said insecticidally effective amount of said composition corresponds to a dose of said compound of between 10 mg and 2 g per 100 $m^2$.

28. A method according to claim 4, wherein said insecticidally effective amount of said composition corresponds to a dose of said compound of between 10 mg and 2 g per 100 $m^2$.

29. A method according to claim 5, wherein said insecticidally effective amount of said composition corresponds to a dose of said compound of between 10 mg and 2 g per 100 $m^2$.

30. A method according to claim 14, wherein said insecticidally effective amount of said composition corresponds to a dose of said compound of between 10 mg and 2 g per 100 $m^2$.

31. A method according to claim 15, wherein said insecticidally effective amount of said composition corresponds to a dose of said compound of between 10 mg and 2 g per 100 $m^2$.

32. A method according to claim 16, wherein said insecticidally effective amount of said composition corresponds to a dose of said compound of between 10 mg and 2 g per 100 $m^2$.

33. A method according to claim 17, wherein said insecticidally effective amount of said composition corresponds to a dose of said compound of between 10 mg and 2 g per 100 $m^2$.

34. A method according to claim 18, wherein said insecticidally effective amount of said composition corresponds to a dose of said compound of between 10 mg and 2 g per 100 $m^2$.

35. A method according to claim 19, wherein said insecticidally effective amount of said composition corresponds to a dose of said compound of between 10 mg and 2 g per 100 $m^2$.

* * * * *